US007283245B2

(12) United States Patent
Xiao et al.

(10) Patent No.: US 7,283,245 B2
(45) Date of Patent: Oct. 16, 2007

(54) HANDHELD DEVICE WITH A DISPOSABLE ELEMENT FOR CHEMICAL ANALYSIS OF MULTIPLE ANALYTES

(75) Inventors: Caibin Xiao, Harleysville, PA (US);
Scott M. Boyette, New Hope, PA (US);
Radislav A. Potyrailo, Niskayuna, NY (US)

(73) Assignee: General Electric Company, Fairfield, CT (US)

( * ) Notice: Subject to any disclaimer, the term of this patent is extended or adjusted under 35 U.S.C. 154(b) by 444 days.

(21) Appl. No.: 10/760,438

(22) Filed: Jan. 20, 2004

(65) Prior Publication Data

US 2005/0157304 A1      Jul. 21, 2005

(51) Int. Cl.
*G01N 21/27* (2006.01)
*G01N 21/47* (2006.01)
*G01N 21/00* (2006.01)
*G06F 19/00* (2006.01)

(52) U.S. Cl. .................. 356/446; 356/445; 356/434; 702/28; 422/82.05

(58) Field of Classification Search ............ None
See application file for complete search history.

(56) References Cited

U.S. PATENT DOCUMENTS

| | | | |
|---|---|---|---|
| 3,799,672 A | 3/1974 | Vurek | |
| 4,050,895 A | 9/1977 | Hardy et al. | |
| 4,225,410 A | 9/1980 | Pace | |
| 4,760,250 A | 7/1988 | Loeppert | |
| 5,114,859 A | 5/1992 | Kagenow | |
| 5,156,972 A | 10/1992 | Issachar | |
| 5,298,428 A | 3/1994 | O'Rourke et al. | |
| 5,340,715 A * | 8/1994 | Slovacek et al. | 250/458.1 |
| 5,525,466 A | 6/1996 | Slovacek et al. | |
| 5,599,668 A | 2/1997 | Stimpson et al. | |
| 5,631,170 A | 5/1997 | Attridge | |
| 5,737,457 A * | 4/1998 | Saini et al. | 250/227.18 |

(Continued)

FOREIGN PATENT DOCUMENTS

JP         2003130791         5/2003
WO       WO 91/13339         9/1991

OTHER PUBLICATIONS

Stewart, G. et al., "Referencing Systems for Evanescent Wave Sensors," *SPIE, Fiberoptics*, (1990), vol. 1314, pp. 262-269.
Jawad, S.M. et al., "Optical Fibre Sensor for Detection of Hydrogen Cyanide in Air—Part 2. Theory and Design of an Automatic Detection System," *Analytica Chimica Acta*, (1991), vol. 246, pp. 259-266, Elsevier Science Publishers B.V., Amsterdam.
Slovacek R.E. et al., "Application of a Plastic Evanescent-Wave Sensor to Immunological Measurements of CKMB," *Sensors and Actuators*, (1995), B 29, pp. 67-71, Elsevier Science S.A.
Kostov, Y. et al., "Low-Cost Optical Instrumentation for Biomedical Measurements," *Review of Scientific Instruments*, (Dec. 2000), vol. 71, No. 12, pp. 4361-4374, American Institute of Physics.
Zolotov, Y.A. et al., "Systems of Measurements and Registration," *Comprehensive Analytical Chemistry, Chemical Test Methods of Analysis*, (2002), pp. 119-138, Elsevier, NY.

*Primary Examiner*—Gregory J. Toatley, Jr.
*Assistant Examiner*—Juan D. Valentin, II
(74) *Attorney, Agent, or Firm*—Wegman, Hessler & Vanderburg

(57) ABSTRACT

A portable system and method for measuring the concentration of multiple chemical or biological substances where an onsite analysis of such substances is needed. The new and original handheld sensor system uses a disposable optical test element and a spectroscopic detector that measures the test element response to specific analytes through a change in light absorbance, luminescence, and other forms of light-based response. In this way, reflection light intensities indicative of the test element response can be used to measure the concentration of the target analytes. The sensor system is also capable of being interfaced to an information processing unit or computer so that analytical data can be manipulated or stored electronically.

6 Claims, 15 Drawing Sheets

U.S. PATENT DOCUMENTS

| | | |
|---|---|---|
| 5,738,992 A | 4/1998 | Cook et al. |
| 5,822,073 A | 10/1998 | Yee et al. |
| 5,830,134 A | 11/1998 | Caputo et al. |
| 5,980,831 A * | 11/1999 | Braiman et al. ............ 385/131 |
| 6,007,775 A | 12/1999 | Yager |
| 6,111,652 A | 8/2000 | Melendez et al. |
| 6,183,696 B1 * | 2/2001 | Elkind et al. ............... 356/445 |
| 6,230,545 B1 | 5/2001 | Adolph et al. |
| 6,328,932 B1 * | 12/2001 | Carter et al. ............ 422/82.06 |
| 6,415,235 B1 | 7/2002 | Bartholomew et al. |
| 6,493,097 B1 * | 12/2002 | Ivarsson .................... 356/630 |
| 6,496,636 B1 * | 12/2002 | Braiman et al. ............ 385/129 |
| 6,528,318 B1 | 3/2003 | Miragliotta et al. |
| 6,788,415 B2 * | 9/2004 | Ogura et al. ................ 356/445 |
| 7,022,288 B1 * | 4/2006 | Boss .......................... 356/301 |
| 7,037,554 B2 * | 5/2006 | Tao et al. ................ 427/163.2 |
| 2003/0075697 A1 | 4/2003 | Ohtsuka et al. |
| 2005/0030543 A1 | 2/2005 | Ohtsuka et al. |

\* cited by examiner

HANDHELD DEVICE WITH A DISPOSABLE ELEMENT FOR CHEMICAL ANALYSIS OF MULTIPLE ANALYTES

FIELD OF INVENTION

This invention relates generally to a method and apparatus for the analysis and measurement of chemical substances by spectrophotometry, and in particular relates to a portable handheld sensor system for the quantitative determination of multiple substances using a disposable optical test element and a spectroscopic detector.

BACKGROUND OF THE INVENTION

It is known that a variety of chemical substances absorb light in proportion to the concentration of the substance present in the sample. Furthermore, the light transmitted through such a substance has an absorption spectrum characterized by the light absorbing properties of the substance and the properties of any other medium through which the light travels. Such absorption spectrum can be prismatically revealed for analysis. By discounting the portion of the absorption spectrum attributable to intensity losses and other absorbers, the spectrum of the chemical substance can be isolated and its identity and concentration determined. The discounting, or "referencing," is done by determining the absorption spectrum of the light source and any spectrophotometric components in the absence of the chemical substance. Referencing is usually done close in time and space to the measurement of the absorbance of the chemical substance to minimize error.

It is well known that portable, battery-powered devices for determining the concentrations of chemical substances are commercially available. Examples include portable photometers provided by Hach Company and portable reflectometers by Merck. A detailed review of photometric and reflectometric systems is given in *Comprehensive Analytical Chemistry, Chemical Test Methods of Analysis*, (Y. A. Zolotov et al., Elsevier, New York (2002)), and in a review paper given in *Review of Scientific Instruments*, (Kostov, Y. and Rao, G., Vol. 71, 4361, (2000)). The adoption of these systems makes chemical analysis outside of a laboratory possible. However, improvements in the following areas are still needed:

1. Some tests with portable instruments use toxic or corrosive reagents.

Some use a large quantity of solid reagents for a single test. For example, many Hach test methods use 200 mg or more solid reagent for a single analyte.

2. An operator has to transfer reagents and sample into a measuring unit.

Sample manipulation and reagent handling are inconvenient parts of chemical analysis and multiply operator-to-operator errors.

3. Liquid waste product resulting from the wet chemistry analysis has to be safely disposed according to applicable laws.
4. Currently available test methods cannot easily determine more than one unrelated analyte in a single test.
5. Although most portable devices have data interpretation and storage capabilities, most test results still need to be transferred manually into a database.

Other methods utilizing test strips have been widely attempted for semi-quantitative analysis for a large number of analytes. Here, quantitative results can be obtained with disposable optical sensor elements, read by a photometer. In most instances, only a single analyte is determined by an optical sensor element. Since transmission absorbance is measured, it is difficult to produce disposable optical sensor elements for calibration free tests.

Disposable chemical sensors are well known in the art. For example, U.S. Pat. No. 5,830,134 describes a sensor system for detecting physico-chemical parameters designed to compensate for numerous perturbing factors, such as those resulting from the use of partially disposable monitoring units, thus eliminating the need for calibration steps.

Another U.S. Pat. No. 5,156,972 discloses a chemical sensor based on light absorption, light emission, light scattering, light polarization, and electrochemically and piezoelectrically measured parameters.

Scatter controlled emission for optical taggants and chemical sensors have been disclosed in U.S. Pat. No. 6,528,318.

Sensor arrays that use reference and indicator sensors are known and described in U.S. Pat. No. 4,225,410. Here, a sensor can be individually calibrated, such that each analysis can be read directly.

U.S. Pat. No. 5,738,992 discloses a method that utilizes a reference material to correct fluorescence waveguide sensor measurements. U.S. Pat. No. 5,631,170 teaches a referencing method for fluorescence waveguide sensors by labeling the waveguide with a reference reagent. It should be pointed out that the internal absorbance standard method used in this invention is fundamentally different from the prior arts in several aspects.

First, the multiangle scatter-induced absorbance detection scheme used in the present invention is different from traditional Attenuated Total Reflection (ATR) sensors that use a thin element with the film thickness approximately the same size as the incident beam wavelength. These thin elements can also include a fluorophore that acts as internal references. In contrast, the present system pertains to thicker film elements that do not require thickness near the incident beam wavelength, and that use alternate internal references based on absorbance.

Two-wavelength, or dual-beam, methods are known in spectrophotmetric analysis. In "Referencing Systems for Evanescent Wave Sensors," (Stewart, G. et al., *Proc. Of SPIE*, 1314, 262 (1990)), a two-wavelength method is proposed to compensate for the effect of contamination on the sensor surface. U.S. Pat. No. 4,760,250 to Loeppert describes an optoelectronics system for measuring environmental properties in which feedback-controlled light sources are used to minimize problems associated with the light source stability and component aging. A similar feedback-controlled two-wavelength method is described in U.S. Pat. No. 3,799,672 to Vurek. A dual-beam reflectance spectrophotometer is described in "Optical Fiber Sensor for Detection of Hydrogen Cyanide in Air," (Jawad, S. M. and Alder, J. F., *Anal. Chim. Acta* 259, 246 (1991)). In Jawad and Alder's method, two LED's are alternately energized. The ratio of outputs at the two wavelengths is used to reduce errors caused by the background absorption of the sensor element for hydrogen cyanide detection. These two-wavelength methods are effective to minimize errors caused by optical and mechanical component aging and long-term stability problems of light sources. However, errors associated with variations in the effective optical pass length of disposable test elements have not been solved.

A disposable sensor system comprising a discardable or disposable measuring device and further comprising one or more sensors is disclosed in U.S. Pat. No. 5,114,859.

Furthermore, analysis of multiple analytes is done with microfabricated sensors as described in U.S. Pat. No. 6,007,775.

In "Application of a Plastic Evanescent-Wave Sensor to Immunological Measurements of CKMB," (Slovacek, R. E.; Love, W. F.; Furlong, S. C., *Sensors and Actuators B*, 29, pp. 67-71, (1995)), it was demonstrated that a sensor handled by non-critical surfaces could be made with improved robustness. These sensing elements were fabricated as blunt-ended plastic cones onto which the sensing chemistries were deposited. The sensing elements were injection-molded from the plastic, making them commercially attractive.

Overall, the known existing sensors have several prominent shortcomings that limit their applicability for field analysis applications. These shortcomings include:

1. Need for critical alignment of testing strip in the sensor to perform accurate reading.
2. Need to reduce errors caused by variations in testing strip quality (imbedded reagent concentrations, effective optical path length, and component aging).
3. Need to reduce errors caused by physical changes in testing elements when they are exposed to a sample, such as swelling, shrinking, or/and crazing.
4. Need for determination of steady-state response in chemical sensor response for accurate analysis.
5. Inability to collect dynamic sensor information from nonreversible chemistries.
6. Inability to collect real-time information from nonreversible chemistries upon exposure to a sample.
7. Inability to analyze the dynamic sensor information from multiple nonreversible chemistries to provide an improved quantification ability of the sensor system.

Because of the above shortcomings in the prior art, a low cost, handheld, and calibration-free sensor system has not been demonstrated. The sensor system disclosed in the present invention is directed toward solution of the above outlined shortcomings. In particular, the sensor in the present invention can collect dynamic information by tracking the rate of change of the kinetic or dynamic response of the non-reversible sensor chemistries as the sample reacts with the sensor in order to quantify the concentration level.

In view of the foregoing, it is an object of the present invention to provide a portable, disposable handheld sensor system for the quantitative determination of analyte concentrations. It is also desirable to provide a system that does not require calibration before each new set of analysis. In this regard, the present system employs dual light analysis on the same sensor element, where sample response is compared with an internal reference, eliminating the need for calibration before each new set of analysis. Moreover, the use of an internal reference significantly reduces the optical and mechanical coupling requirements for the device, thereby providing cost advantage in the manufacturing and assembly process with minimal impact on the accuracy of testing results It is a further object of this invention to provide a sensor that is capable of communicating with an information processing unit, for example a pocket personal computer or wireless mobile phone or a satellite, so that analytical data can be manipulated, transmitted, or stored electronically.

It is important to note that the present invention provides a general photometric and/or spectroscopic test method where no liquid reagent is needed. This not only simplifies the test, but also reduces costly and labor-intensive requirements related to the handling and disposal of toxic reagent material.

SUMMARY OF THE INVENTION

The present invention provides a portable, disposable handheld sensor system for measuring analyte concentrations in chemical substances. The system provides a general photometric and/or spectroscopic test method where no liquid reagent is needed and that does not require calibration before each new set of analysis. Major components of the system include thin film sensing reagents immobilized on a disposable test element, an adapter for mounting the test element in a reproducible manner, and a light source, which is capable of exciting a photometric response from the test element. Accordingly, the system includes commercially available optical light source and photodetector elements, in combination with appropriate coupling devices, fixturing, power supplies, and electronic circuitry, allowing the system to interface and transmit data to a computer or other display, storage, or processing unit. The system also contemplates additional apparatus to support its major functions, such as a closure to isolate the test element from ambient light during the sensing measurement. It is also understood that the invention provides a highly responsive sensor system that can be expanded to measure a plurality of analytes with a single multisectional test element, and that can be easily carried to virtually any location where onsite analysis of chemical or biological samples is needed. Examples of such a location include a remote lake or stream, or a cooling tower on the roof of a tall building.

The present invention and its advantages over the prior art will become apparent upon reading the following detailed description and the appended claims with reference to the accompanying drawings.

DETAILED DESCRIPTION OF THE INVENTION

The present invention pertains to a method and apparatus for measuring the concentrations of chemical substances by utilizing the reactive properties of certain chemical substances; for example, the property of the substance to react with another chemical, e.g., a select analyte, causing a chemical change in the first reagent, and resulting in a change in the light absorbing properties of the original chemical-containing material. In operation, the present invention measures the test element response to specific analytes through a change in light absorbance, luminescence, light scattering, or other light-based response. The analytes described in this invention are chemical species, but this invention can also be envisioned to include biological systems where bioanalyte interactions stimulate similar test element response. As an example, such biological systems could be immobilized enzymes that stimulate light response proportional to an analytes concentration, for example, luciferase response to adenosine triphosphatase (ATP).

Figure 1:
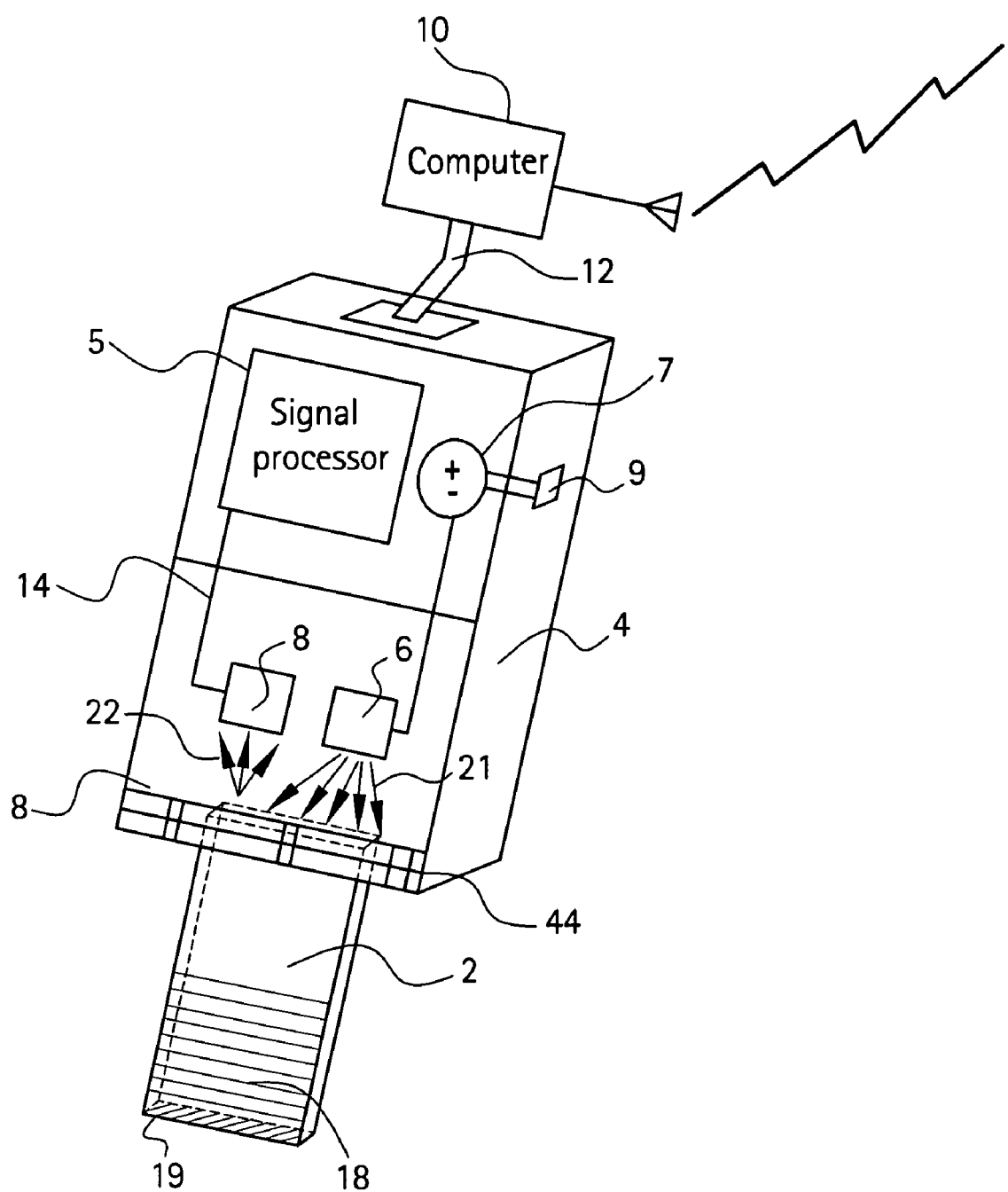
FIG. 1 is a perspective view of a handheld sensor system according to an embodiment of the present invention.

With reference now to the drawings, FIG. 1 shows a basic sensor system comprising a disposable test element 2, which is approximately the size of a glass microscope slide, detachably mounted onto adapter 4. The test element 2 is made of any reasonably transparent substance such as glass or organic polymeric material that has a refractive index ($n_1$) that is usually greater than unity. A portion of the test element is coated on one or both sides with a thin, transparent polymer film containing reagents that are needed to react with analytes in order to produce a color product. The reagent film can be immobilized onto the test element by dip coating or spin coating the test element, or by other means known in the art. In addition to coating a portion of the test element, it is understood that the entire test element may be coated as well. In combination with the above mentioned reagent substance, the reactive film coating also includes a reference dye which serves to provide an internal light absorbance standard, or internal reference, whereby the refractive index of the reagent-dye film mixture ($n_2$) can be less or more than $n_1$. The reference dye is mixed together with the film coating to provide a reagent film complex having a constant internal light absorbance standard. In other words, the reference dye component of the reagent film complex provides a first light absorbance response, and the reagent itself provides a second light absorbance response, allowing the reagent film complex to provide a dual light absorbance response (i.e. dual light response) to incident light energy. However, unlike the reagent itself, the reference dye does not react with the analyte. Accordingly, the dye's spectral profile would remain constant from one test element to another, and before and after the test element is exposed to the sample, if the optical and mechanical properties of the test element have not changed. Moreover, since the reference dye and reagent have different light absorbance spectrum, the reference dye's spectral profile does not appreciably overlap with the target detection wavelength, or range of wavelengths, used to measure the test element response to the reaction between reagents and the analyte. By providing such a non-overlapping benchmark response differential between the reference dye and the reagent, the reagent film complex provides an internal light absorption standard or internal reference, thus providing an internal dual light response which eliminates the need for external calibration and device calibration before each new set of analyses. As discussed in more detail below, it is understood that the internal reference also minimizes response variation from device to device, providing substantial manufacturing and maintenance cost advantage with minimal impact on the accuracy of test results. As a consequence, the characteristics and features of the present system are well suited for cost effective production, assembly, and miniaturization. The internal reference cited above is a colorimetric dye, but this is just one of many possible embodiments. Any standard that does not react with the analyte detection chemistry and that has a spectral response outside the detection spectra can act as an internal standard. This material can be an inorganic complex, a pigment, dye, or micro- or nanoparticle that produces the desired spectral response and can be used to correct the errors due to film variations.

Referring again to FIG. 1, the mounting adapter 4 comprises at least one light source 6, which can be any means that is capable of emitting light energy 21, such as LED, laser diode, or miniature light bulb. The adapter 4 further comprises at least one photodetector 8, which can be any means that is capable of detecting light energy 22 and converting said energy to electrical output signals that are indicative of the test elements response to the target analyte or analytes. These electrical output signals are transmitted to signal converter 5 via circuit wire 14. It is understood that many commercially available photodetectors could be used to achieve the desired performance, such as photodiode, micromachined photo multiplier tube, or photocell, and are well known in the art.

The adapter 4 also includes fixturing means 44 serving to align the test element 2 and locate it in a reasonably reproducible position with respect to the light source 6 and photodetector 8. As discussed in more detail below, the present invention does not require fixturing means 44 to provide strict positioning and control of the test element. Rather, it has been discovered that a modest or reasonable control of the test element 2 with respect to the light source and photodetector is effective to achieve accurate and reproducible absorbance results, thereby offering cost advantage in the manufacturing, maintenance, and assembly requirements.

Figure 3:
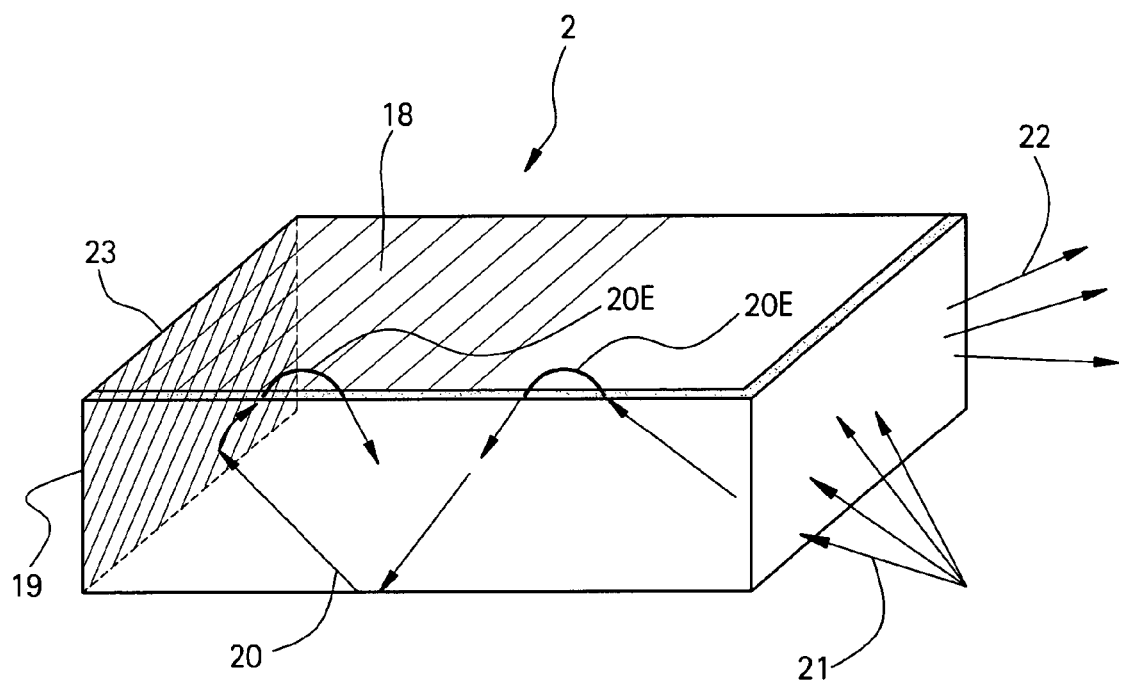
FIG. 3 is a perspective view of a disposable test element according to an embodiment of the present invention.

In operation, with power switch 9 activated, the light source 6 produces an uncollimated and unfocused light beam. As best shown in FIG. 3, the uncollimated and unfocused light beam impinges the test element at different angles; that is, at angles less than and greater than the critical angle of the test element. As discussed in more detail below, a portion of this incident light energy reacts with the reagent film complex immobilized on the test element. Once such incident light energy passes through the reagent film complex, the photodetector is capable of detecting a pair of light response spectra; that is, the photodetector detects a first light response from the internal reference dye alone, and a second light response from the reagent film itself, thereby allowing the device to detect a dual light response from the incident light-test element interaction. In this way, any changes in the test element light response spectra can be detected and measured without the need for external calibration before each new set of analysis. Furthermore, it will be shown that due to the uncollimated and unfocused nature of the incident light beam, strict control and positioning of the test element by fixturing means 44 is not required to provide relatively accurate test results. Rather, fixturing means 44 need only provide a modest or reasonable positional control for the test element 2, thereby providing cost savings in the manufacturing process.

The adapter 4 further comprises battery 7 to power the sensor system; although skilled artisans will appreciate that many alternative means to power the sensor system may be used as well. In addition, suitable electronic means are provided which allow the signal converter 5 to communicate with signal processing unit 10 so that the electrical output signals generated by the photodetector 8 can be processed and stored electronically. It is understood that many well-known configurations can be utilized in a manner known in the art to achieve the same performance as the above embodiment, including an embodiment capable of communicating via interface 12 with an external processing unit 10, for example a handheld computer, PDA, or other wireless transmission device. Moreover, it is understood that an embodiment comprising a built-in processing unit (not shown) could be used as well.

By way of example, and not by way of limitation, the light source 6 is positioned proximate an edge of the detachable test element 2 so that incident light waves 21 emitted from the light source impinge an edge 23 of the test element, where the uncollimated and unfocused light beam from the light source impinges the test element at a plurality of different angles as best shown in FIG. 1. It is well known that a critical angle of the test element may be calculated from the refractive index of the substrate ($n_2$) and that of air ($n_1$) through equation $\Theta_c = \sin^{-1}(n_2/n_1)$, where $\Theta_c$ is the critical angle. Referring now to FIG. 3, a divergent light beam 21 is directed toward the edge of the test element at approximately 45°. Since the light beam 21 is unfocused and uncollimated, some of the incident photons 21 impinge the test element 2 at angles greater than the critical angle, while other incident photons impinge the test element at angles less than the critical angle. In the event that the incident angle of the photons 21 is greater than the critical angel $\Theta_c$, the light beam will be totally reflected at the film-air interface. This phenomenon is called total reflection. On the other hand, if the incident angle of the light beam 21 is less than $\Theta_c$, the incident light beam will be partially reflected at the film-air interface. This phenomenon is called partial reflection.

In the case of total reflection, although a portion of the light beam 21 will be totally reflected at the film-air interface of the test element, a portion of the reflected light energy can penetrate into the film and reenter the substrate as if it has traveled a short distance parallel to the interface. This energy is called an evanescent field or evanescent wave 20E as shown in FIG. 3. Since a reactive film coating 18 has been immobilized onto the surface of the test element, a portion of the evanescent wave 20E will be absorbed (attenuated) by the film coating 18 at the substrate-film interface. This phenomenon is called attenuated total reflection (ATR). In the case of partial reflection, the partially reflected photons of the incident light beam 21 are similarly capable of forming an evanescent wave 20E and becoming absorbed by the film coating, while the remaining un-reflected photons may be lost into the surrounding environment. This phenomenon is called Attenuated Partial Reflection (APR). To increase the effectiveness of APR, a reflective coating 19 can be immobilized onto an end of the test element, whereby un-reflected incident light 20 that has penetrated into the body of the test element may reflect against the reflective coating 19 and scatter back through the test element. Consequently, a portion of these internally reflected photons 20 are provided with another opportunity, or "second chance", to form an evanescent wave and react with the film coating 18 at the surface of the test element. Accordingly, since the present invention includes components from both ATR and APR, it is possible to improve the efficiency of the incident light beam 21 without the need for costly optical devices or coupling requirements, thereby providing advantage over well-known ATR systems.

Referring again to FIG. 3, as the evanescent light wave 20E propagates along the surface of the test element, a portion of these evanescent photons are able to interact with molecules contained in the reactive film 18. This interaction causes a portion of the evanescent photons to become absorbed by the molecular structure of the reactive film. Accordingly, the photons 22 that were lucky enough to avoid becoming absorbed by the reactive film 18, and were not otherwise lost to the environment, will be transmitted from the test element where they may be ultimately detected by the photo detector 8. Since the number of photons 22 that are ultimately transmitted from the test element depends upon the absorbance level of the incident light beam 21, it is possible to utilize electrical signals generated by the photo detector to indicate the absorption percentage of the reactive film. Once the relative intensity of the ultimate light response is compared with known reference data, it is possible to detect and determine the analyte concentration of the sample substance.

Figure 5:
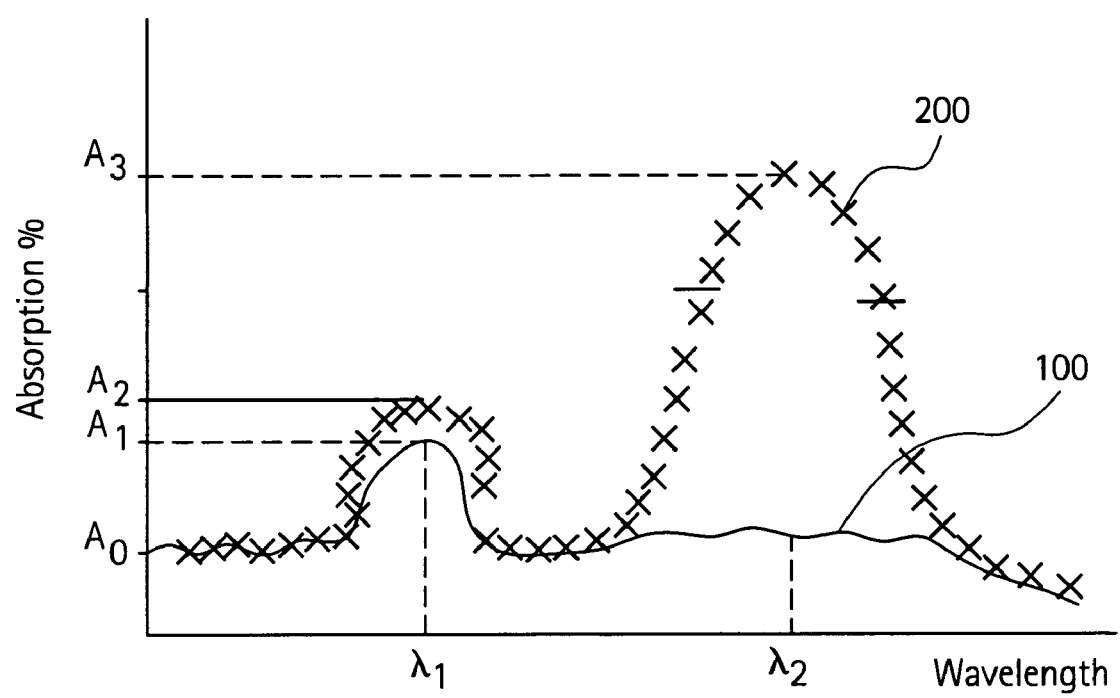
FIG. 5 is an example of a dual wavelength response from a single analyte.

As described above, when power switch 9 is activated and light beam 20 is projected onto the test element, the photo detector receives a dual light response 22 from the test element. Such response curve is illustratively shown in FIG. 5. Here, line 100 represents the light response of the film coating before the test element is exposed to the sample analyte, and line 200 represents the dual light response of the film coating after the test element is exposed to the sample analyte. $A_0$ represents the absorption level of the film coating alone at wavelength $\lambda_2$. The first peak at $A_1$ represents the absorption level of the internal reference dye at wavelength $\lambda_1$ before exposure, and $A_2$ represents the absorption level of the internal reference after exposure. Values of $A_1$ and $A_2$ would be the same, if the optical and mechanical properties of the test element have not changed during the exposure. The peak at $A_3$ represents the absorption level of the film coating at wavelength $\lambda_2$ after the test element is exposed to the sample analyte. If it is known that the sample substance absorbs light in proportion to the concentration of the substance present in the sample, it can be shown that the difference between the absorption levels $A_3$ and $A_0$ is proportional to the analyte concentration of the sample substance. By taking into account the absorbance levels ($A_1$ and $A_2$) of the internal reference centered at $\lambda_1$, it is possible to calibrate the absorbance levels of the reagent film coating according to the general formula:

$$A_{corrected} = A_3 - A_0 + (A_1 - A_2), \quad (1)$$

where $A_{corrected}$ represents the normalized absorbance level of the reagent film coating. It is understood that many alternative procedures, such as comparing peak-to-peak ratios or areas under the curve could also be used to normalize the response curve.

In order to calculate absorbance, blank signal outputs at $\lambda_1$ and $\lambda_2$ of the test element before a reagent film is coated have to be known. The signal sensor response can be obtained by measuring the photodiode signal when a test element without the polymer film is loaded. The blank response can be stored in the processor. It will become clear in the following section that the final result $A_{corrected}$ is independent of the blank response. Knowing the blank response allows the absorption level of the test element before exposure to be expressed as absorbance unit rather than volts or amperes measured by the photodiode.

In a preferred mode of operation, the polymer coated test element 2 is detachably mounted to the adapter 4 by fixturing means 44. As described above, fixturing means 44 aligns and locates the test element in a reasonably reproducible position with respect to the light source and photodetector. Strict control of the incident light angle and test element with respect to the light source and photodetector is not required. In order to compensate for variable lighting conditions, once at the sample test site the operator activates the light source to record the corresponding reflection intensities from the coated test element. The light response spectra measured during this step are referred to as baseline intensities.

After the baseline intensity response is established, the operator proceeds to expose the coated test element to the chemical or biological sample substance for a given period of time, for example 1-3 minutes, depending on the diffusivity of the film coating. Next, the operator removes the test element from the sample, and excess liquid sample is allowed to run down or off the test element. This step may take 0-5 minutes. After this period, the operator again activates the light sources to record the corresponding reflection intensities from the sample exposed test element. The light responses measured during this step are referred to as sample intensities.

Continuing the above analysis, the accumulated data representing the blank, baseline, sample and internal reference response intensities are processed and combined with known chemical reference data corresponding to the expected spectral response of a particular analyte under inspection. As shown and discussed in more detail in Examples 1-5 below, by comparing the intensity of the light response after the test element is exposed to the analyte with the intensity of the light response before the test element is exposed to the analyte, it is possible to measure the analyte concentration of the sample substance.

The system described above shows photometric measurement carried out with conventional optical devices. As a result of the multiangle scatter-induced absorbance measurement technique utilized by the present invention, it is possible to achieve accurate, reproducible absorbance measurements for films with higher sensitivity than is possible with traditional transmission measurement techniques for these films. This is because traditional transmission absorbance measurement techniques can be characterized as "one pass"; that is, incident photons in traditional transmission techniques get "one pass" through the substance under inspection, allowing the photons a single opportunity to react with the test element as they propagate through the substrate with minimal refraction and scattering. In contrast, as best shown in FIG. 3, the present invention utilizes a multiangle scattering approach whereby incident photons 21 scatter inside the test element and reflect against the reflective coating 19, thereby allowing a portion of the incident photons to have "multiple passes" through the test element. This multiangle scattering approach increases the likelihood that evanescent photons 20E will ultimately react with the film coating on the surface of the substrate. As such, if an incident photon fails to evanesce the surface of the substrate on its initial pass, there is a high probability that the same photon will scatter inside the test element and ultimately reflect back towards the surface of the substrate, thus providing such photon with another opportunity to evanesce the surface of the substrate and ultimately become absorbed by the film coating. Accordingly, it is possible for a given amount of light energy to achieve a larger proportion of absorption events compared to traditional transmittance techniques, thereby increasing the relative absorbance percentage of the incident light, and improving the ultimate sensitivity of the sensing device.

It is important to note that many configurations of the same major components can achieve the same performance as the above embodiment. For example, another embodiment of the present invention is illustratively shown in FIG. 2. Here, there is shown a multisectional optical test element 2A comprising separation regions 3 and sensing regions 5. The separation regions act as barriers between the sensing regions by absorbing scattered light that may become reflected at the several sensing regions, thereby reducing interactive noise between the sensing regions. Each sensing region utilizes an independent reactive film coating comprising its own internal chemistry. Each of these reactive film coatings and their accompanying chemistries are effective to provide an independent dual light (spectral) response from a particular analyte of interest in the sample solution. Accordingly, a plurality of analytes can be simultaneously tested on a single test element. Moreover, it has been discovered that the separation regions 3 can be perforated for improved separation, thereby increasing the effectiveness of the test element.

To facilitate operation of the multisectional test element, it is contemplated that an independent light source and photodetector pair can be provided for each of the independent sensing regions, whereby each source and detector pair is capable of generating an appropriate dual light response from each of the several sensing regions. Alternatively, a single light source and photodetector may be configured to generate and detect a suitable dual light (spectral) response from each of the independent sensing regions. In this case, the independent electrical signal generated by each of the several sensing regions can be combined and multiplexed in a manner known in the art by processing unit 10 to detect and quantify a plurality of analytes with a single disposable test element.

Figure 4:
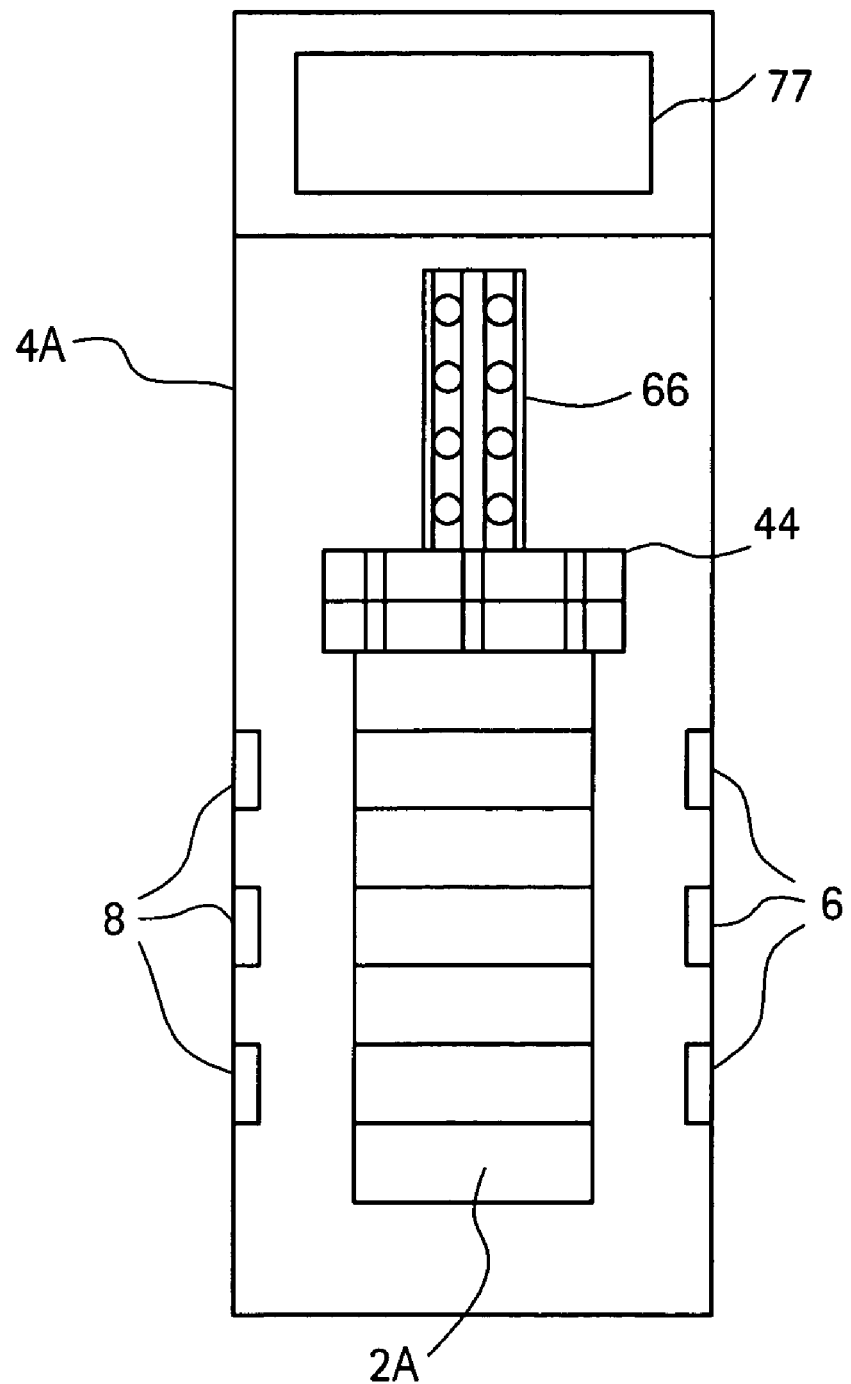
FIG. 4 is a perspective view of a handheld sensor system according to an embodiment of the present invention using a multisectional test element.

FIG. 4 describes an apparatus to facilitate the multisectional test element. This apparatus has the same basic components as for the system shown in FIG. 1. The exemplary embodiment of FIG. 4 comprises several pairs of light sources 6 and photodetectors 8 which can be mounted on the two sides of adapter 4A. The multisectional test element 2A is mounted onto the fixturing means 44. Here, the fixturing means 44 is attached to a mobile carriage of miniature motion slide 66. The motion slide allows the test element to be retrieved inside the adapter and serves to align the test element with the light source/photodetector pairs for absorbance measurements. Suitable electronic means 77 are provided for controlling the device so that electrical output signals generated by the photodetectors can be processed and stored electronically.

The present invention also contemplates the utilization of additional sensors that could be used to provide information about the ambient atmospheric conditions such as temperature (for example, using a thermister), relative humidity (for example, using a capacitance humidity sensor), and atmospheric pressure (for example, using a MEMS pressure sensor) and are well known in the art.

In another embodiment, the chemical sensor system contemplates a dynamic pattern recognition system for improving the functionality and quantitative ability of the sensor array. The functionality of the sensor array is improved by having means of indicating the end of the required environmental exposure of the sensor. For example, the sensor is immersed into a water sample until an alarm (for example, a sound beep) indicates that the sensor is ready to be withdrawn and is ready to provide quantitative information. The operative principle of such system is based on the use of the dynamic signal analysis of the sensor response. In particular, the sensor in the present invention can collect dynamic data during a specified time period by tracking the rate of change of the response of the non-reversible sensor chemistries as the sample reacts with the sensor in order to quantify the concentration level. Thus, our sensor is more information-rich compared to the sensors that are simply exposed to a sample and further withdrawn when the signal measured after the withdrawal. This collected dynamic data can be analyzed for known parameters such as initial, intermediate, and final slope of signal during exposure. These dynamic parameters can be used to indicate when a steady-state response is reached. If the steady state cannot be reached in a reasonable period, the dynamic parameters can be used to quantify the analyte concentration. Additionally, the slope of the chemical sensor response can be more sensitive than the equilibrium end point, and result in increased sensitivity for the sensor system described here.

In yet another embodiment, the sensor has another alarm that indicates the time of analysis completion after the sensor is withdrawn from the sample. This data is provided by different signal recovery rates from different sensor regions, which are dependent on the sensor chemistry, reversibility, and ambient atmospheric conditions. As skilled artisans will appreciate, many suitable electronic, integrated circuit and/or microprocessor means may be configured to provide the above-mentioned sensor and timer alarm features to obtain the collection of dynamic sensor response data of the contemplated embodiments described above. In one embodiment shown in FIG. 15, a Visual Basic® computer program was developed to provide the timer and alarm features and to control and read the sensor system.

It is well known that reversible chemical sensors often suffer from poor response selectivity, and this is primarily due to interference or noise from non-specific signal changes. Accordingly, the selectivity of chemical recognition can be improved with non-reversible, disposable sensors. Non-reversible sensor chemistry often provides stronger and more selective interactions between the reactant and the chemical species of interest, and this is generally viewed as one of the advantages created by non-reversible sensor chemistry. However, if it is advantageous to improve the sensor's dynamic range or reduce chemical interferences, it may be desirable to analyze a single analyte using several sensor regions containing different reagents, or complimentary sensor elements that in combination enhance the overall system response. Despite the known disadvantage associated with reversible reagents, one can include a reversible reagent in a multi-reagent detection scheme to improve the overall sensor response. This combination of a reversible and non-reversible platform can create a system with enhanced capabilities. Standard pH indicators are one example of chemicals commonly used in reversible sensors while the chlorine reagent described in the following examples is an example of nonreversible chemistry. As a non-limiting example, combining a reversible pH sensor with a non-reversible chlorine sensor makes it possible to further define other chlorine-containing species present in the sample.

With reference now to the following examples, it has been discovered that a modest or reasonable control in the coupling and positioning requirements of the test element and optic components, as opposed to a strict or critical control of such coupling and positioning requirements, is effective to achieve accurate and reproducible absorbance results if an internal reference absorbance standard is used according to the following equation:

$$A_{corrected} = A_{sample} - A_{baseline} + (A_{baseline\_at\_\lambda_{reference}} - A_{baseline\_at\_\lambda_{sample}}). \quad (2)$$

However, it is recognized that utilizing a single internal absorbance standard does not remove all the errors caused by variation in film or substrate quality and the alignment of the test element with respect to the incident beam. This is because each error source has a different effect on the absorption bands at different wavelengths. For example, a change in absorbance caused by a change in the angle of incidence is a function of wavelength, not chemistry, since the optical path length is dependent on wavelength. Thus, it is recognized in the present invention that using a referencing system with more than one internal standard can increase accuracy or by using the spectral profile of a single standard absorption band if whole spectra are measured. But it is important to note that a reasonably high level of reproducible measurement has been achieved by utilizing a single internal absorption standard in combination with a modest or reasonable mechanical control coupling between the disposable test strip and adaptor, as demonstrated by the following examples.

EXAMPLE 1

Figure 6:
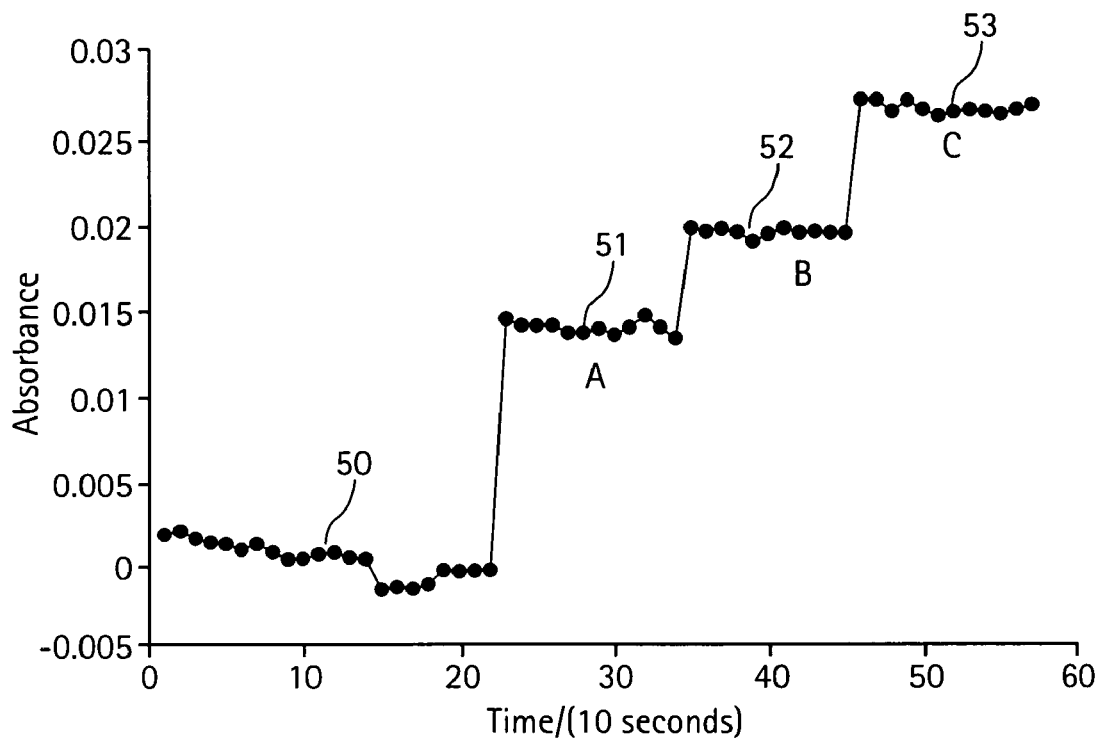
FIG. 6 is an example of a series of absorption levels showing a change in spectral response from exposure of different concentrations of ink to light.
Figure 14:
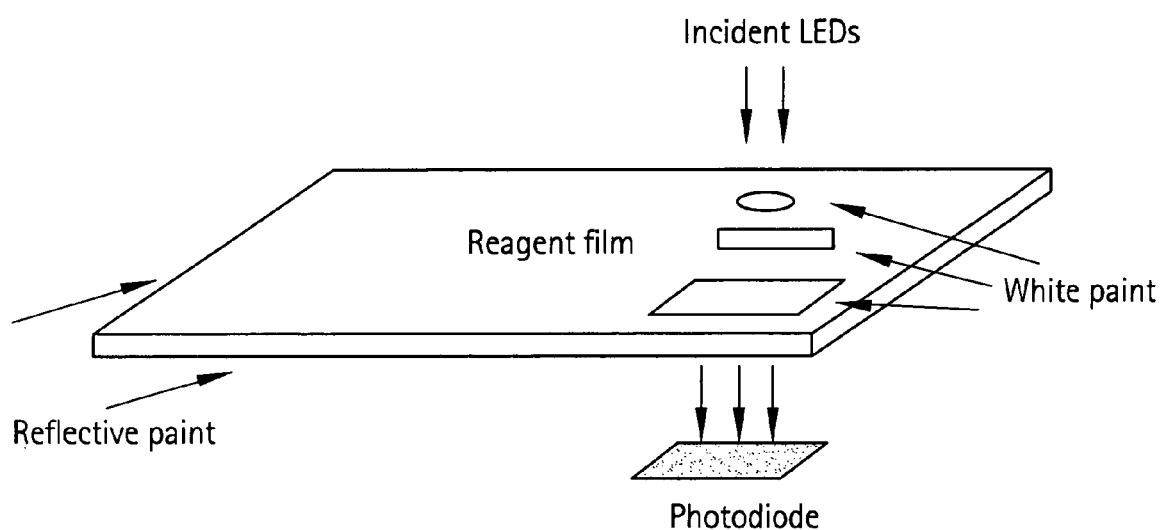
FIG. 14 is a schematic description of the measurement configuration used for Example 1.

Four edges of a Fisher brand, clear glass slide (dimensions 3"×1"×0.41", Fisher catalog number 12-549) were painted with a white paint pen (Uni®Paint PX-20) as shown in FIG. 14. An area near one end was also painted with the white paint pen. The arrangement of LED and photocell is shown in FIG. 14. The light source was a 5 mm, 3000 mcd red LED, with peak emission wavelength at 660 nm and a viewing angle 12° available from RadioShack®. Absorbance levels of different concentrations of blue lines made with a permanent, fine point Sharpie® marker are shown in FIG. 6. Here, during the initial time interval 0-22 seconds, light was projected onto a blank (no blue marking) glass slide. As expected, the corresponding absorbance level shown at line 50 is approximately zero. After approximately 22 seconds, a single blue line was made on the glass slide, and the corresponding absorbance level increased to line 51 as shown. After approximately 34 seconds, a second blue line was made on top of the first blue line to increase the concentration of blue marking on the glass slide. As expected, the corresponding absorbance level increased to line 52. Similarly, after approximately 45 seconds, a third blue line was added to further increase the concentration of blue marking on the glass slide. Again as expected, the corresponding absorbance level increased to line 53. It is well known that the absorbance for this measurement is defined as:

$$A = \log[(\text{photocell output for a clear glass slide-output at dark})/(\text{output for blue lines-output at dark})]; \quad (3)$$

where output at dark is the steady state response of the detector when the light source is turned off.

Figure 2:
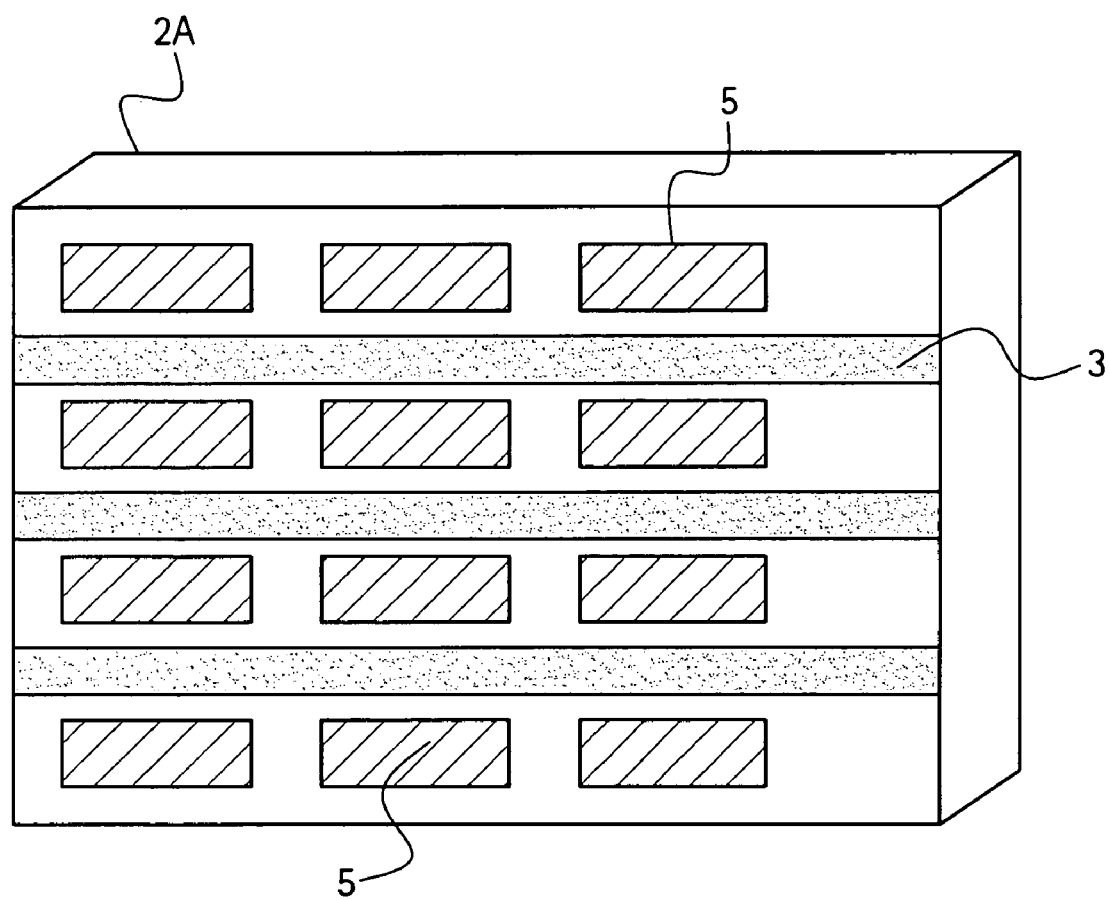
FIG. 2 is a frontal view of a multisectional disposable optical element according to an alternative embodiment of the present invention.

This example demonstrates that photometric measurements may be conducted in a very simple manner. However, many designs can be built from this simple setup. For example, interference filter films can be coated in the areas facing the photodetector or mixed into the reflective paint so that absorbance for a given absorption band can be measured. FIG. 2 illustrates one of these designs.

EXAMPLE 2

Figure 7:
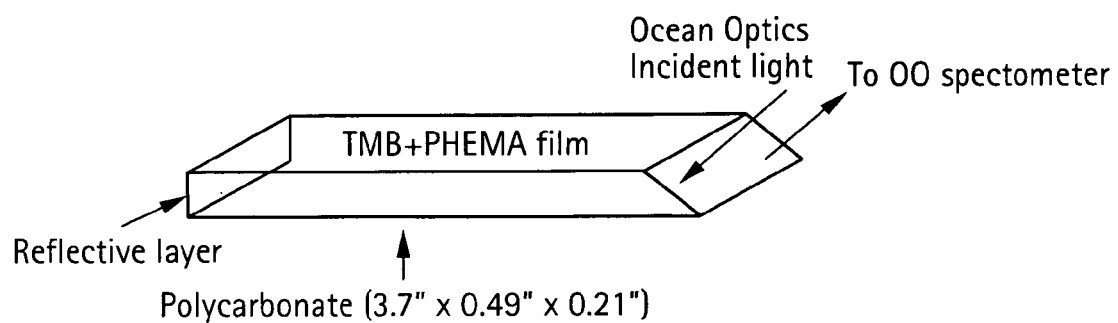
FIG. 7 is a perspective view of another measurement configuration according to an example presented by the present invention.
Figure 8:
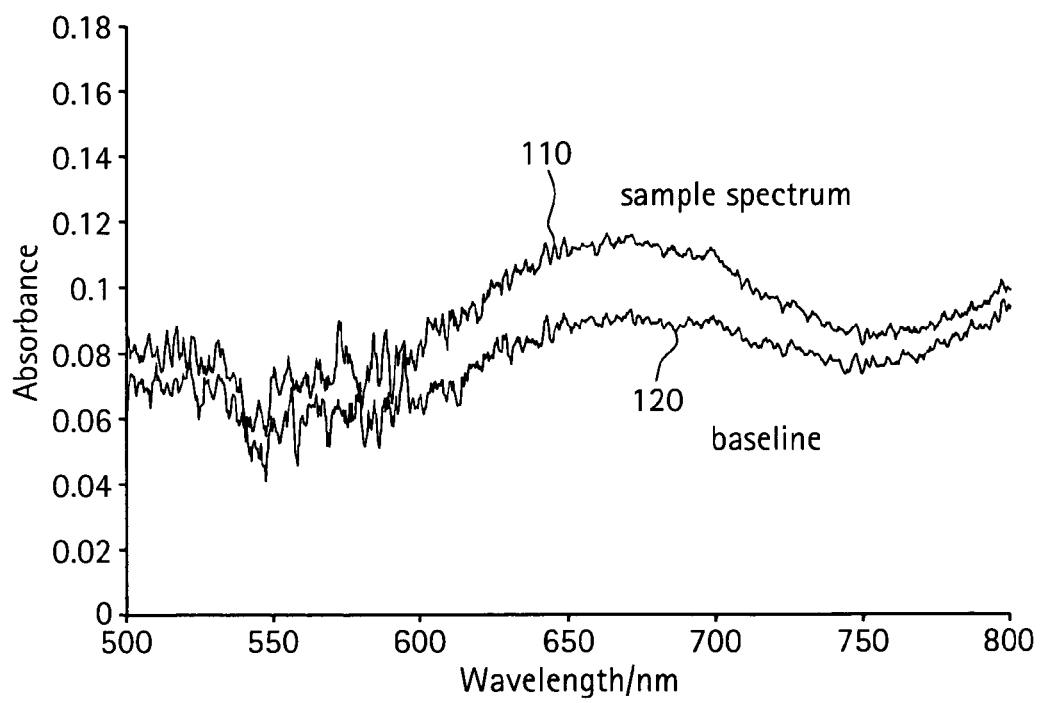
FIG. 8 is an example of a baseline spectrum and sample spectrum obtained with a polycarbonate reflection element.

In this second example, a 3.7"×0.49"×0.21" polycarbonate reflection element was made. An end of the polycarbonate element was beveled to an angle equal to approximately 51°. The test element configuration for absorbance measurement used in this example is shown in FIG. 7. Here, an Ocean Optics P400-2 six optical fiber bundle was used to provide the incident light from an Ocean Optics tungsten-halogen lamp. An R400-7 Ocean Optics reflection probe was used to collect the reflected light to an Ocean Optics USB2000 spectrometer. Before a poly (2-hydroxylethyl methacrylate) (PHEMA) film containing tetramethylbenzidine (TMB) was dip coated on one side of the polycarbonate element, a blank spectrum with zero absorbance for all wavelengths was established. After the TMB film was coated, the polycarbonate element was put back to the configuration as shown in FIG. 7. Here, a baseline spectrum was first recorded. Next, a 0.06 ml 0.1 ppm sodium hyperchlorite solution was carefully spread to cover a 3 mm×12 mm area over the TMB film. After staying on the TMB film for 1 minute, NaOCl solution was carefully removed with aid of a paper towel. The sample spectrum was measured 4 minutes after the NaOCl solution was spotted on the TMB film. Both the sample spectra 110 and baseline spectra 120 are shown in FIG. 8.

EXAMPLE 3

The same Ocean Optics spectrometer system from Example 2 was used in this example. A microscope slide holder tightly controlled the positioning of the glass slide. The incident optical fiber probe was directed to one side of the glass slide at roughly 45° angle with respect to the glass slide plane. About half of the incident light illuminated the white paper underneath the glass slide and the other half illuminated an edge of the glass slide. The detection probe was also angled at about 45° and the distance from the probe to the slide was adjusted so that the amount of light does not saturate the spectrometer.

A PHEMA film containing a small amount of red dye was recovered from a permanent red Sharpie® marker. A solution of red dye was spin coated on glass slides as in Example 1 with a spinner modified from a magnetic stirrer, which does not have speed control or readout. The spinner acceleration, the final spin speed, and spinning duration were not controlled. The red dye is used as the internal absorbance standard. It has an absorption band centered at $\lambda_{max}$=535 nm, which does not overlap the absorption band of the TMB reaction response to chlorine (blue reaction product, $\lambda_{max}$=670 nm).

Before the slides were immersed into NaOCl solution, a baseline spectrum for the TMB was measured. After a 90-second immersion in the NaOCl solution, the glass slide was removed and held at a vertical position for 2 minutes so that solution on the glass slide surfaces could run down. Here, the sample spectrum was recorded 150 seconds after the glass slide was removed from the NaOCl solution.

A total of 11 slides were used according to the above procedure to measure the absorbance values at three different concentration levels of NaOCl solution. Slides 1-4 were independently immersed into an 0.10-ppm solution, slides 5-7 were independently immersed into an 0.25-ppm solution, and slides 8-11 were independently immersed into an 0.50-ppm solution. The absorbance values at $\lambda$=650 nm before and after reference correction are listed in Table 1 below. It is important to note that the standard deviation for each concentration level is significantly reduced after reference correction was performed according to equation 1.

TABLE 1

Absorbance values before and after reference correction.

| | | Before Correction | | After Correction | |
|---|---|---|---|---|---|
| NaOCl/ppm | Slide# | Absorbance | Average +/− standard deviation | Absorbance | Average +/− standard deviation |
| 0.1 ppm | 1 | 0.047 | 0.041 ± 0.015 | 0.057 | 0.053 ± 0.004 |
| | 2 | 0.057 | | 0.049 | |
| | 3 | 0.021 | | 0.051 | |
| | 4 | 0.038 | | 0.056 | |
| 0.25 ppm | 5 | 0.168 | 0.151 ± 0.015 | 0.095 | 0.100 ± 0.008 |
| | 6 | 0.146 | | 0.096 | |
| | 7 | 0.140 | | 0.109 | |
| 0.05 ppm | 8 | 0.206 | 0.188 ± 0.018 | 0.181 | 0.179 ± 0.003 |
| | 9 | 0.192 | | 0.181 | |
| | 10 | 0.163 | | 0.175 | |

Figure 9:
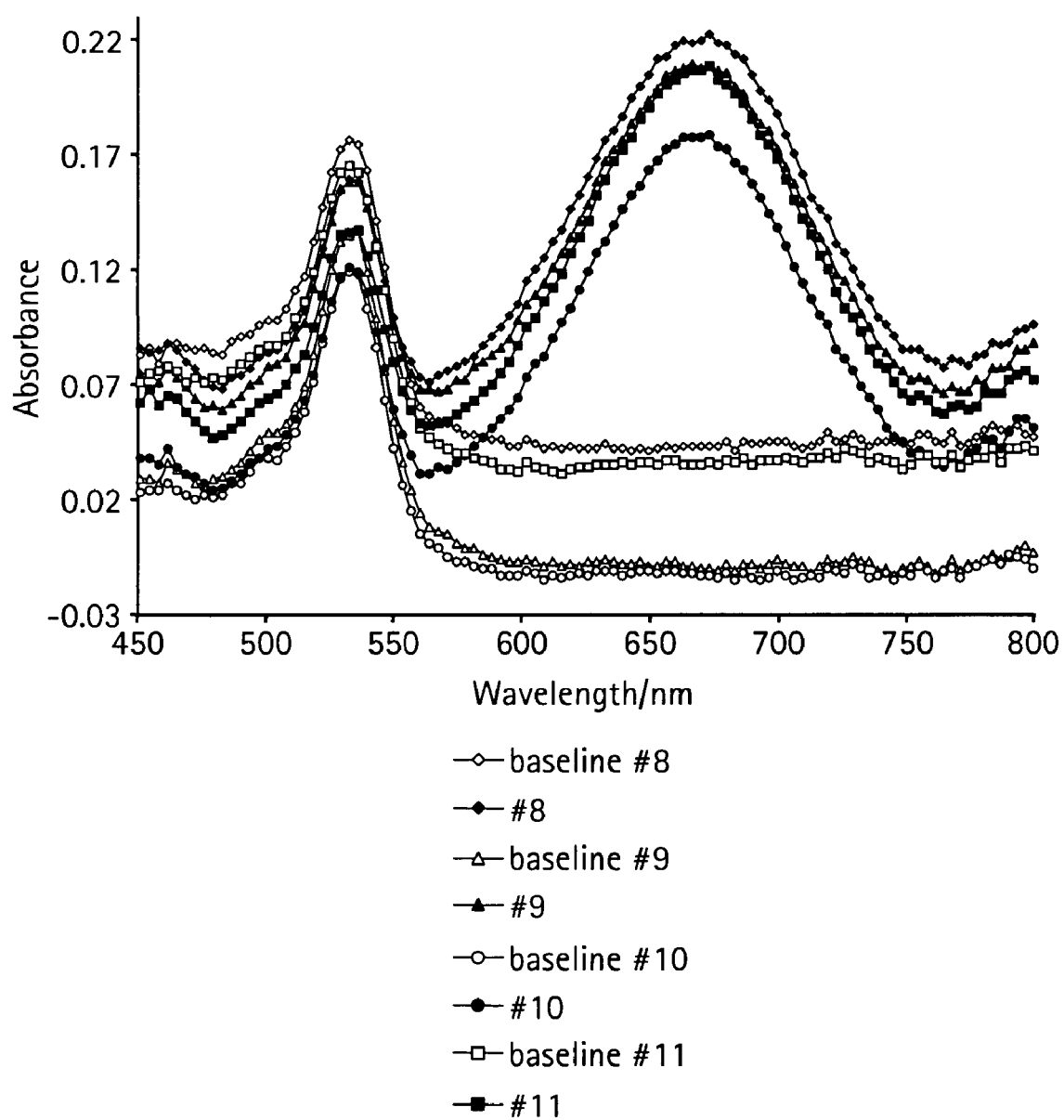
FIG. 9 is an example of a sample spectra for 0.5 ppm NaOCl before reference corrections and whereby the optical element position was tightly controlled.

The four spectra from slides 8-11 and their corresponding baseline spectra are presented in FIG. 9.

Figure 10:
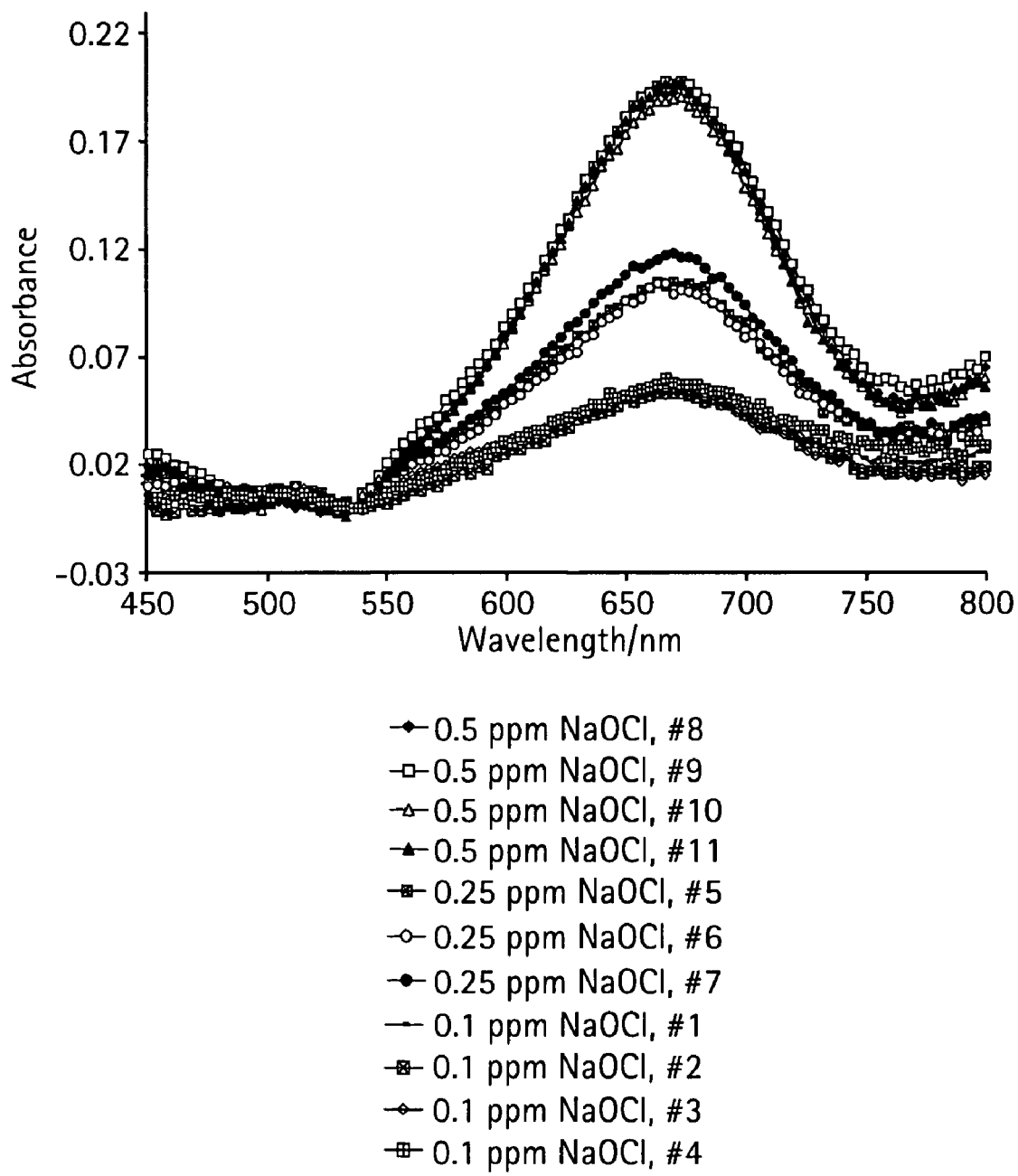
FIG. 10 is an example of a sample spectra for 0.5 ppm NaOCl after reference correction and whereby optical element position was tightly controlled.

All 11 spectra after reference correction according to equation 1 are shown in FIG. 10. FIG. 10 graphically demonstrates that normalizing the results according to the internal absorbance standard, as described by equation 1, reduces error and confirms the results listed in Table 1.

Figure 11:
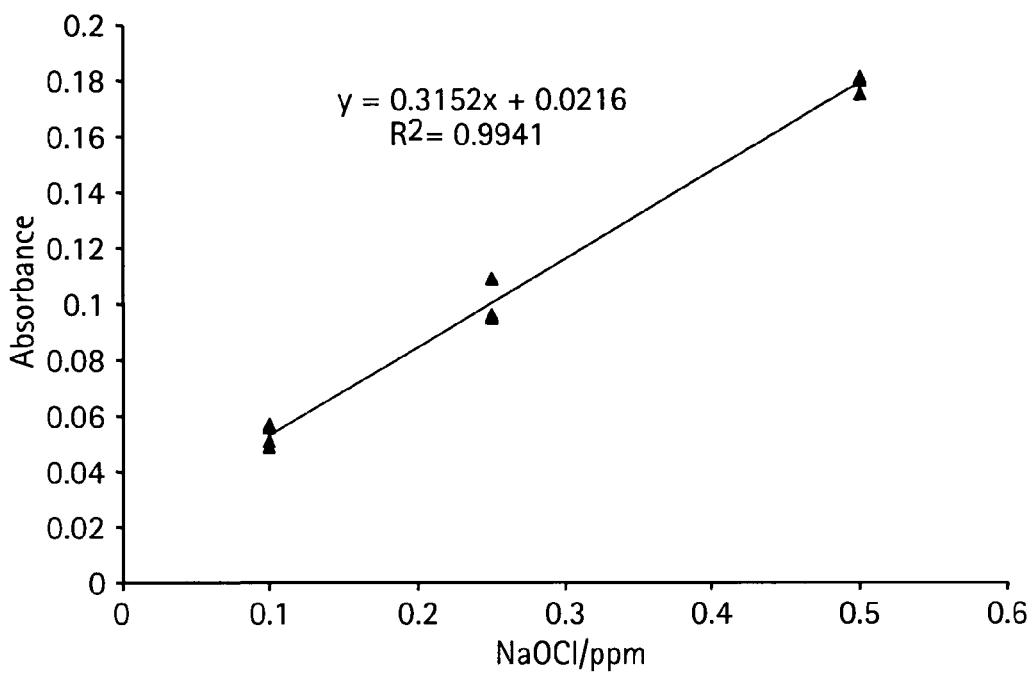
FIG. 11 is an example of a calibration curve for reference corrected absorbance listed in Table 1.

FIG. 11 shows a calibration curve confirming the linear relationship between absorbance levels and concentration levels as known in the art.

Several conclusions can be drawn from the results obtained in this example:

1. Appropriate positional control alone does not ensure the accuracy needed for low absorbance measurements.

2. Using an internal absorbance standard to correct spectra according to equation 1 reduces errors caused by variations in experimental parameters such as glass slide dimension, film quality, and incident beam angle.
3. Multiangle scatter-induced absorbance is more sensitive than transmission absorbance. In comparison with the transmission absorbance value at λ=535 nm (0.014), a 10-fold increase in absorbance is achieved with the multiangle scatter-induced configuration of the present invention. It is important to note that even greater increases can be expected with longer wavelengths.

EXAMPLE 4

The films used in this example contained a slightly lower concentration of the internal reference dye compared to the films used in Example 3. These films were prepared by the same procedure used in Example 3, but were produced in a different batch. Similarly, the experimental setup was the same as used for Example 3, except the slide position was only loosely controlled by aligning the slide with respect to two (2) perpendicular lines drawn with a Sharpie® marker.

Figure 12:
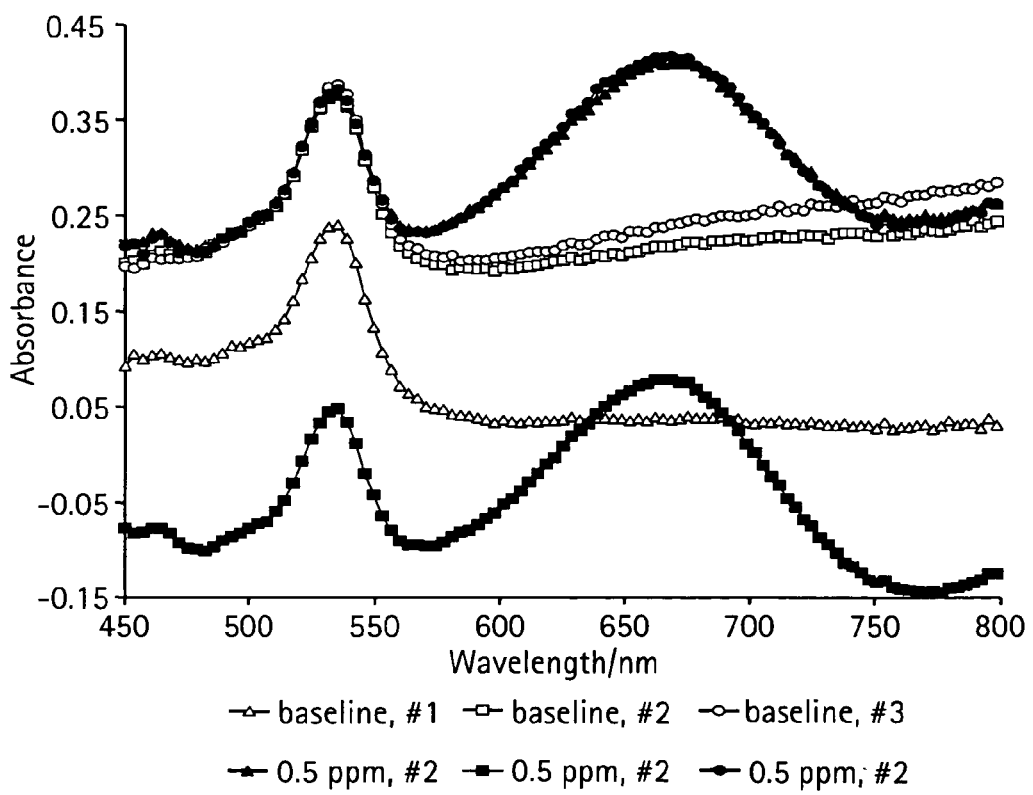
FIG. 12 is an example of a sample spectra for 0.5 ppm NaOCl before reference correction and whereby optical element position was not tightly controlled.
Figure 13:
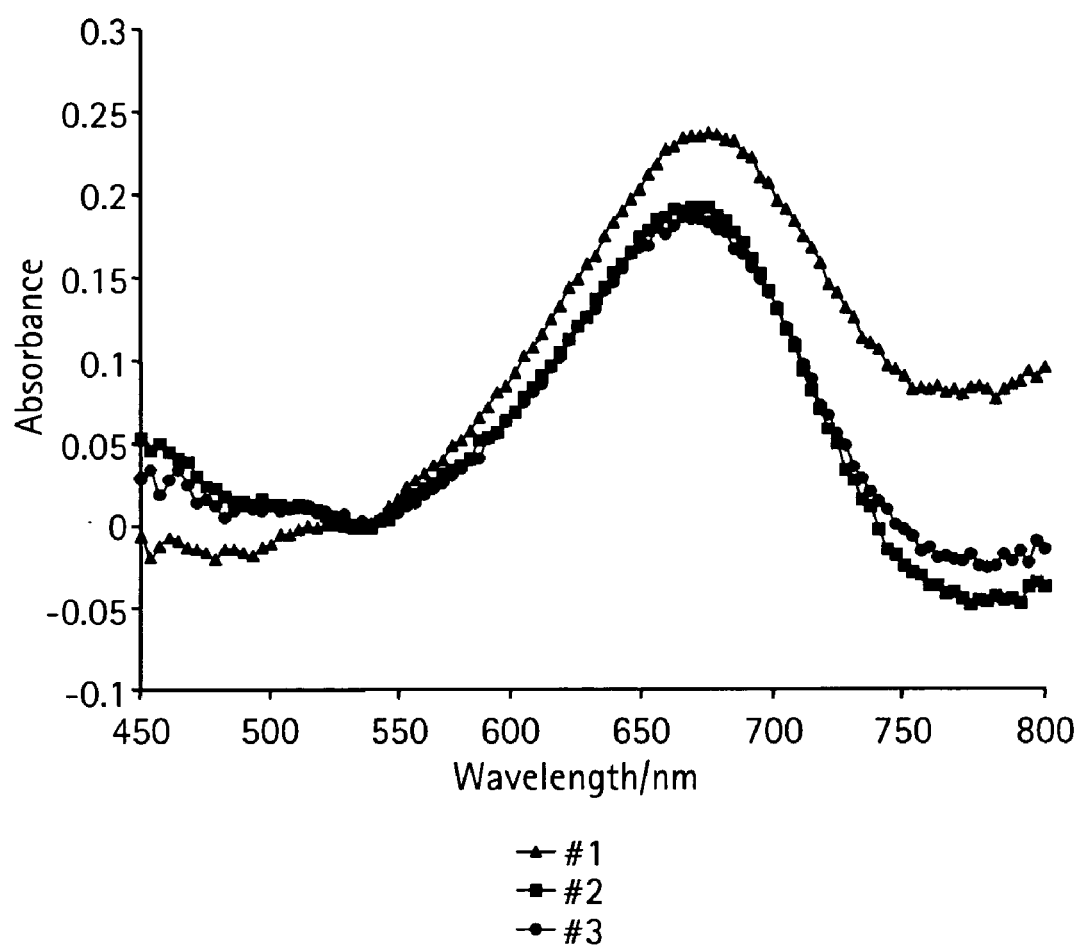
FIG. 13 is an example of a sample spectrum for 0.5 ppm NaOCl after reference correction and whereby optical element position was not tightly controlled.

The spectra response before and after reference correction together with baseline spectra response are shown in FIGS. 12 and 13 respectively. It is evident that measurements derived without maintaining appropriate control of the glass slide position results in a larger margin of error, despite the reference correction from the internal absorbance standard. Nevertheless, it is important to note that the absorbance values at 650 nm 0.177, 0.185, and 0.209 agree well with the average values of 0.179±0.003 obtained from Example 3, even though the slide position was not tightly controlled and the films were prepared in a different batch and from a different polymer solution. This agreement is significant, especially in view of one objective of the present invention; that is, to provide for the quantitative determination of analyte concentrations by way of a disposable test element, without an additional calibration step.

EXAMPLE 5

Sensor Construction

Figure 15:
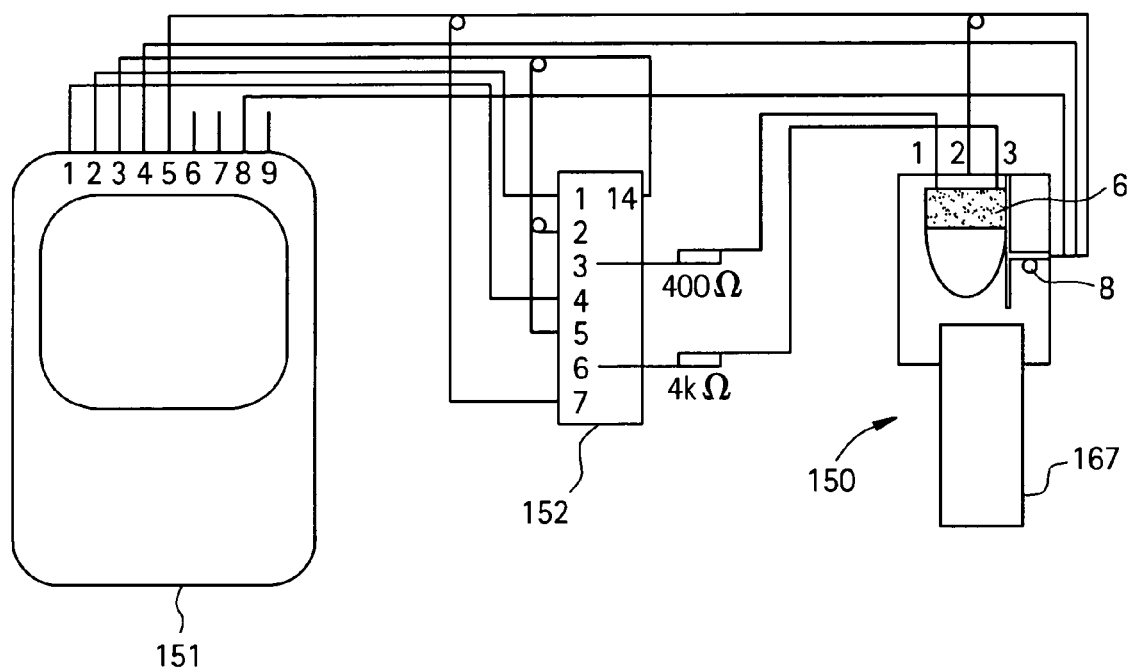
FIG. 15 is a schematic description of the handheld sensor system for Example 5.

A schematic diagram of an exemplary handheld sensor system used for Example 5 is shown in FIG. 15. Here, the basic sensing unit 150 is shown connected to digital bus switch 152 (Texas Instruments, SN74CBTLV) and computer 151 (Dell Axiom Pocket PC equipped with Dataq CF2, C-Cubed Limited data acquisition card). The digital bus switch 152 was used to allow the computer to turn ON and OFF the LED 6 while providing DC power to the photodiode 8, and allowing the output from the photodiode to be read. A Visual Basic® computer program was developed to control and read the sensor system.

Figure 16:
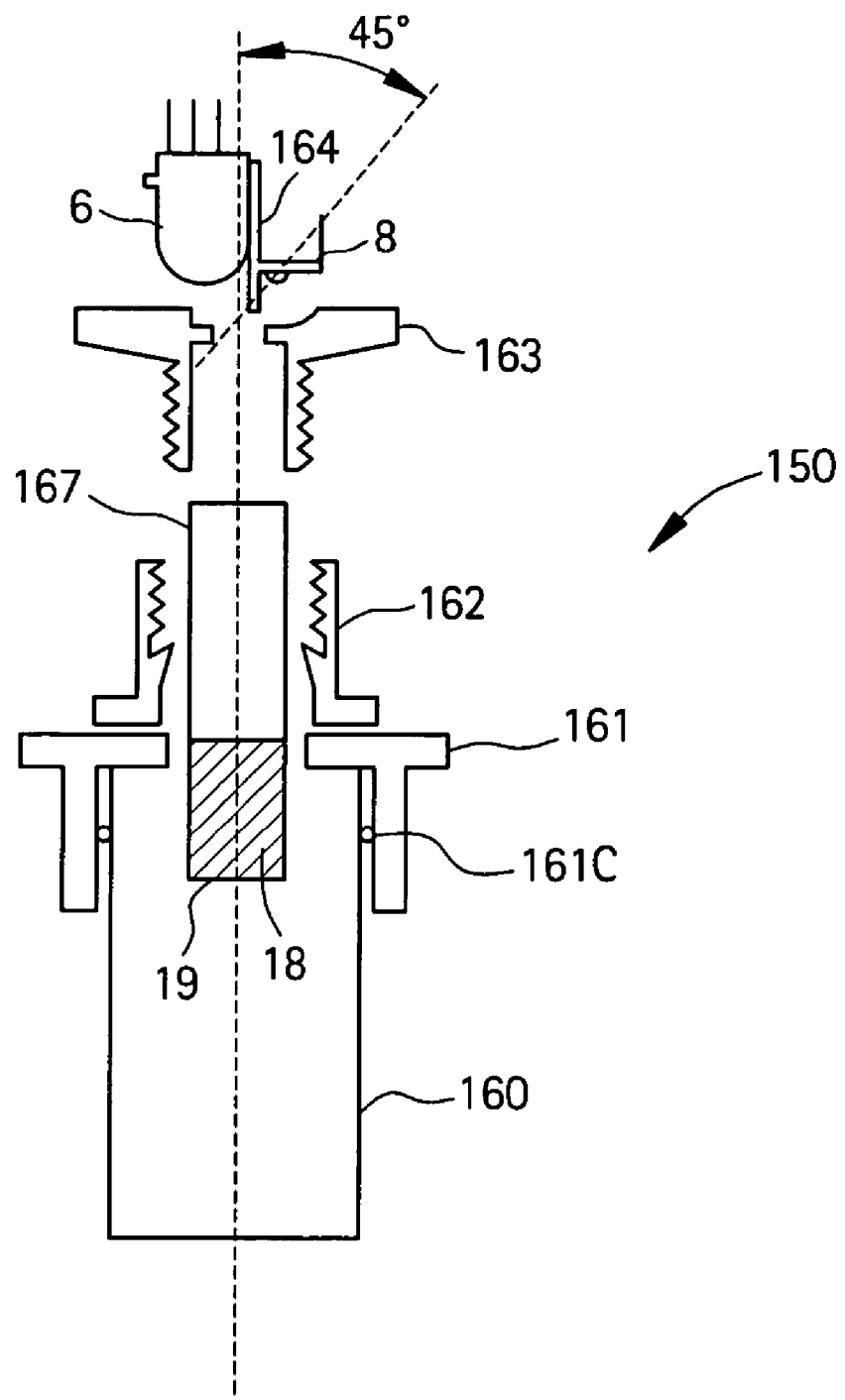
FIG. 16 is a perspective view of the handheld sensor for Example 5.

A perspective diagram of an exemplary sensing unit 150 used for Example 5 is shown in FIG. 16. Here, the sensing unit 150 can be described as comprising a combination of three sub-assemblies: Part A; Part B; and Part C.

Part A comprises elements 160, 161, and 162. Part B comprises elements 6, 8, 163, and 164. Part C comprises elements 18, 19, and 167.

In constructing Part A, the threaded part of a ½-inch instant tube-to-pipe adapter 161 was removed and a ¼-inch compression fitting nut 162 was glued onto the face of the modified adapter 161. A 4-inch long, ½ OD stainless steel tube 160 is inserted onto the rubber O-ring/compression fitting 161C of the modified adapter to provide a light tight compartment.

In constructing Part B, the male part of a ¼ inch tube-to-pipe compression fitting 163 was removed, and a thin polycarbonate sheet 164, which was painted black on one side, was fixed to the modified fitting with epoxy glue so that the opening of the modified fitting is divided as best shown in FIG. 16. A 5 mm bicolor LED 6 (LC LED N500TGR4D) was glued onto the polycarbonate sheet. The focal path of the LED 6 is approximately parallel to the vertical center of the fitting 163. A photodiode 8 (Toas TSR257) was attached to the other side of the polycarbonate sheet so that the collection lens of the photodiode is offset from the axis of the fitting with an angle of about 45° as shown in FIG. 16. After the above construction, the LED and photodiode were sealed inside a 1-inch diameter PVC tube (not shown in FIG. 16).

In constructing Part C, an acrylic rod (0.25 inch diameter and 3.20 inch long) 167 was coated with PHEMA film containing chlorine sensitive reagents 18 as used in Example 3. The end section of the rod was painted with reflective white paint 19.

Measurement Procedure

The measurement procedure used for Example 5 comprised the following steps:
1. (a) Load the acrylic rod 167 (Part C) into the compression fitting assembly (Parts A and B) and put the stainless steel tube 160 into the instant tube-to-pipe adapter 161; (b) Click the button on the Pocket PC screen; (c) The Visual Basic® computer program turns on the green (525 nm) and red lights (630 nm) sequentially, and takes respective readings ($G_o$ and $R_o$) from the photodiode while the green and red lights are turned ON.
2. (a) Remove the stainless steel tube 160 from the adapter 161 and dip the rod 167 into a sample solution for 60 seconds; (b) Pull the rod from the solution and remove remaining solution with a suitable wipe; (c) Let the rod dry for two minutes in air.
3. (a) Put the stainless steel tube 160 back onto the adapter 161; (b) Click the appropriate button on the Pocket PC screen to read respective outputs G and R from the photodiode. Note that both the green and red light are turned ON sequentially.
4. Calculate absorbance with equation 2.

$$A = \log(R_o/R) - \log(G_o/G) \quad (2)$$

Figure 17:
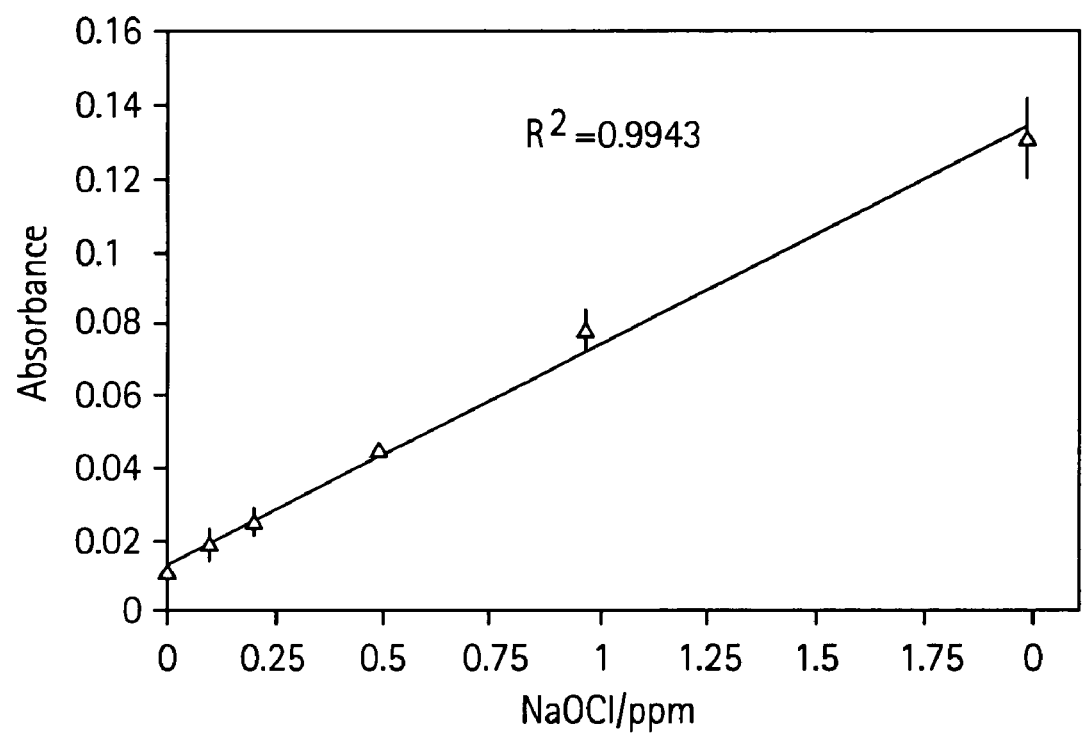
FIG. 17 is a calibration curve obtained with the handheld sensor described in Example 5.

Note that equation 2 is mathematically equivalent to equation 1. The results from these measurements are listed in Table 2 and plotted as a calibration curve in FIG. 17.

TABLE 2

Results for Example 5

| NaOCl/ppm | $R_o$/V | $G_o$/V | R/V | G/V | Absorbance |
|---|---|---|---|---|---|
| 0.00 | 1.873 | 1.762 | 1.852 | 1.780 | 0.009 |
| 0.00 | 1.937 | 1.829 | 1.895 | 1.835 | 0.011 |
| 0.00 | 2.055 | 1.941 | 2.002 | 1.944 | 0.012 |
| 0.096 | 1.960 | 1.867 | 1.891 | 1.864 | 0.015 |
| 0.096 | 2.079 | 1.965 | 1.939 | 1.928 | 0.022 |
| 0.096 | 1.946 | 1.847 | 1.808 | 1.802 | 0.021 |
| 0.20 | 1.998 | 1.843 | 1.835 | 1.809 | 0.029 |
| 0.20 | 1.916 | 1.835 | 1.816 | 1.827 | 0.022 |
| 0.20 | 1.936 | 1.846 | 1.805 | 1.824 | 0.025 |
| 0.49 | 1.964 | 1.847 | 1.732 | 1.805 | 0.045 |

TABLE 2-continued

Results for Example 5

| NaOCl/ppm | $R_o$/V | $G_o$/V | R/V | G/V | Absorbance |
|---|---|---|---|---|---|
| 0.49 | 1.995 | 1.875 | 1.756 | 1.831 | 0.045 |
| 0.49 | 1.855 | 1.780 | 1.646 | 1.752 | 0.045 |
| 0.97 | 1.926 | 1.806 | 1.556 | 1.743 | 0.077 |
| 0.97 | 1.979 | 1.871 | 1.615 | 1.808 | 0.074 |
| 0.97 | 1.936 | 1.852 | 1.525 | 1.772 | 0.084 |
| 1.99 | 1.901 | 1.805 | 1.360 | 1.695 | 0.118 |
| 1.99 | 1.957 | 1.868 | 1.340 | 1.754 | 0.137 |
| 1.99 | 1.899 | 1.806 | * | * | 0.136 |

*data were missed

While the specification above has been drafted to include the best mode of practicing the invention as required by the patent statutes, the invention is not to be limited to that best mode or to other specific embodiments set forth in the specification. The breadth of the invention is to be measured only by the literal and equivalent constructions applied to the appended claims.

What is claimed is:

1. A method for measuring analyte concentration of a chemical or a biological substance, said method comprising the steps of:
   a. providing a reagent film with at least one internal reference standard;
   b. immobilizing a layer of said film onto a test element, thereby providing a film coated test element;
   c. emitting light energy onto a coated test element, wherein said light energy undergoes internal reflection and multiangle scattering inside said test element, said light energy being effective to stimulate a dual reference light response from said coated test element;
   d. exposing said coated test element to a sample substance for a specified time period, then removing said exposed test element from said substance, thereby providing a sample test element;
   e. emitting light energy onto said sample test element, said light energy being effective to stimulate a dual sample light response from said sample test element;
   f. collecting and processing said reference and sample light response data to calculate a light absorption response;
   g. utilizing said light absorption response to detect and quantify analyte concentration in said substance; and
   h. generating a signal indicative of said analyte concentration based on said detection and quantification.

2. The method of claim 1 further comprising the step of collecting dynamic data from said light absorption response during a specified time period.

3. The method of claim 2 further comprising the step of analyzing said dynamic data for determining initial slope, intermediate slope, and final slope of said light absorption response during said time period.

4. The method of claim 1 wherein said light absorption response is error corrected by normalizing said light absorption response.

5. The method of claim 4 wherein said normalizing is performed according to the formula: $A_{corrected} = A_{sample} - A_{baseline} + (A_{baseline\_at\_\lambda_{reference}} - A_{baseline\_at\_\lambda_{sample}})$.

6. The method of claim 1 wherein said coated test element is a multisectional test element capable of providing a plurality of said light absorption responses, said plurality of said light absorption responses being processed and multiplexed in order to detect and quantify a plurality of analyte concentrations in said substance.

* * * * *